US010495607B2

(12) United States Patent
Putkaradze et al.

(10) Patent No.: US 10,495,607 B2
(45) Date of Patent: Dec. 3, 2019

(54) SENSOR INCLUDING MECHANICAL RESONATOR WITH NANO-STRUCTURED SURFACE

(71) Applicants: Vakhtang Putkaradze, Edmonton (CA); Arindam Phani, Edmonton (CA); Prashanthi Kovur, Edmonton (CA); Thomas Thundat, Edmonton (CA)

(72) Inventors: Vakhtang Putkaradze, Edmonton (CA); Arindam Phani, Edmonton (CA); Prashanthi Kovur, Edmonton (CA); Thomas Thundat, Edmonton (CA)

(73) Assignee: 2033668 ALBERTA LTD, Calgary, Alberta (CA)

( * ) Notice: Subject to any disclaimer, the term of this patent is extended or adjusted under 35 U.S.C. 154(b) by 98 days.

(21) Appl. No.: 14/995,998

(22) Filed: Jan. 14, 2016

(65) Prior Publication Data

US 2016/0209369 A1    Jul. 21, 2016

Related U.S. Application Data

(60) Provisional application No. 62/104,294, filed on Jan. 16, 2015, provisional application No. 62/173,195, filed on Jun. 9, 2015.

(51) Int. Cl.
*G01N 29/036* (2006.01)
*G01N 33/00* (2006.01)
*G01N 29/02* (2006.01)

(52) U.S. Cl.
CPC ......... *G01N 29/036* (2013.01); *G01N 29/022* (2013.01); *G01N 33/0027* (2013.01);
(Continued)

(58) Field of Classification Search
CPC ... G01N 29/036; G01N 29/022; G01N 33/027
(Continued)

(56) References Cited

U.S. PATENT DOCUMENTS 5,741,961 A       4/1998  Martin et al.
8,377,683 B2 *    2/2013  Lu .......................... B82Y 5/00
                                                       119/300
(Continued)

OTHER PUBLICATIONS

International Search Report dated Mar. 14, 2016 in application PCT/IB2016/050181.
(Continued)

*Primary Examiner* — Nimeshkumar D Patel
*Assistant Examiner* — Rodney T Frank
(74) *Attorney, Agent, or Firm* — Foley & Lardner LLP

(57) ABSTRACT

A dissipation-based sensor includes a single resonator with a nano-structured surface. The sensor exhibits improved sensitivity, up to about 2 orders of magnitude higher than a single resonator without a nano-structured surface. The sensor operates by measuring and estimating the fluid friction per oscillation cycle, operating in normal conditions without vacuum (e.g., in air or other ambient gas) at room temperature. The sensor can provide measurement data at a speed that is orders of magnitude faster than pre-existing resonance-based methods, as it is based on measurements from a few cycles only. The dissipation-based sensor may be utilized in a broad range of fast, inexpensive, hand-held measuring devices. Additionally, the sensor is capable of operating at standard temperature and pressure.

19 Claims, 17 Drawing Sheets

(52) U.S. Cl.
 CPC ............... *G01N 2291/0215* (2013.01); *G01N 2291/02809* (2013.01)

(58) Field of Classification Search
 USPC ........................................................ 73/24.06
 See application file for complete search history.

(56) References Cited

U.S. PATENT DOCUMENTS

| | | | |
|---|---|---|---|
| 8,846,551 B2* | 9/2014 | Gupta .................... | B23K 26/12 438/795 |
| 2011/0036151 A1 | 2/2011 | Andle et al. | |
| 2011/0127445 A1* | 6/2011 | Zhang ................ | A61K 41/0071 250/459.1 |
| 2014/0015548 A1* | 1/2014 | Naughton .............. | G01R 27/26 324/658 |

OTHER PUBLICATIONS

Ivanoff Reyes et al. "A ZnO Nanostructure-Based Quartz Crystal Microbalance Device for Biochemical Sensing." IEEE Sensors Journal, vol. 9, No. 10, Oct. 2010. pp. 1302-1307.

Sabri et al. "Electro-deposition of Gold Nano-Structures on Gold Quartz Crystal Microbalance (QCM) Electrodes for Enhanced Mercury Vapor Sensitivity in the Presence of Interferent Gases." International Conference on Nanoscience and Nanotechnology, Feb. 25-29, 2008, pp. 71-74.

Zhang et al. "ZnO Nanotip-based QCM Biosensors." IEEE International Frequency Control Symposium and Exhibition, Jun. 2006, pp. 545-549.

\* cited by examiner

SENSOR INCLUDING MECHANICAL RESONATOR WITH NANO-STRUCTURED SURFACE

CROSS-REFERENCE TO RELATED APPLICATIONS

This application claims priority to and the benefit of U.S. Provisional Patent Application No. 62/104,294, filed on Jan. 16, 2015, and U.S. Provisional Patent Application No. 62/173,195, filed on Jun. 9, 2015. The entire disclosures of U.S. Provisional Patent Application No. 62/104,294 and U.S. Provisional Patent Application No. 62/173,195 are incorporated herein by reference.

BACKGROUND

The present application relates generally to the field of mechanical resonance based sensors for use in sensing the presence of, for example, environmental contaminants.

The technique of mechanical resonance based detection and sensing at micro/nano scales has been shown to be capable of achieving resolutions equivalent to that of a proton mass. Such sensors rely on the frequency shift and/or amplitude change of a very narrow-band resonator. A measurable response change may be obtained by overcoming damping effects, which are detrimental in this context. The primary aim in the design of resonator-based sensing has previously been to minimize all dissipative effects.

Dissipation may result both from viscous friction with the fluid media that interacts with the sensor and also from internal losses of the material, the former being typically dominant in mechanical resonator systems. Minimization of viscous damping has been achieved by operating the system in high vacuum, but the inevitable presence of air in the system prevents the complete elimination of viscous damping. This viscous friction becomes more of a concern with the miniaturization of the systems to the sub-micron and nanoscales, which are intended to attain higher sensitivities and resolution. The wide practical application of such systems with a consistent high vacuum and low temperatures is uneconomical and impractical.

The study of the dissipation in micro-cantilevers for sensing purposes has also been considered. The dissipation in the cantilever is influenced by changes in the media, such as addition of other gases and the attachment of microorganisms (e.g., *Bacillus anthracis*) to the cantilevers. These studies were based on measuring the dissipation and corresponding frequency shift exhibited by a single resonator. For such a single-resonator system, the relative change of dissipation and subsequent change of frequency is proportional to the relative change of kinematic viscosity. The use of dissipation itself in such systems presents a challenge as it reduces the quality factor of the resonator, and limits the ability to measure the corresponding frequency shift. For example, a relative change in viscosity by 1% will lead to a corresponding change in dissipation of about 1% as well. In addition, using this method, it is difficult to obtain a good selectivity of the device.

It would be advantageous to produce an improved sensor incorporating a single mechanical resonator. The improved sensor provides increased sensitivity at reduced cost. These and other advantages will be apparent to those reviewing the present disclosure.

SUMMARY

An exemplary embodiment relates to a sensor including a resonator and a nanostructure comprising a plurality of elements that is disposed on a surface of the resonator. The nanostructure is configured to move through a media to be sensed. Other exemplary embodiments include systems incorporating such sensors and methods of using such sensors and systems.

The resonator included in the sensor may be a cut quartz crystal resonator. The nanostructure may be disposed on an electrode surface of the resonator. The plurality of elements of the nanostructure may include nanotubes or nanorods, such as ZnO nanorods. The elements may have a diameter of about 20 nm to about 60 nm, and may have a length of about 300 nm to about 900 nm. The elements may be spaced apart by about 20 to about 200 nm, and may have an element density of about 15 to about 25 elements per $\mu m^2$.

The resonator may be disposed within a sensor housing. The sensor housing may include a sensor chamber in which the plurality of elements of the nanostructure extend such that they may move in relation to the media to be sensed. An impedance analyzer may be configured to measure the dissipation of the resonator. The impedance analyzer may be a dedicated circuit disposed within the sensor. The sensor may include an infrared radiation source configured to irradiate the media to be sensed, and the infrared radiation source may be an infrared diode. The sensor may also include a power source. The sensor may be capable of driving the resonator at a variety of amplitudes or across a range of driven amplitudes.

Another exemplary embodiment relates to a sensor including a resonator and a nanostructure including a plurality of elements disposed on a surface of the resonator. The nanostructure is configured to move through a media to be sensed. The resonator may be a cut quartz crystal resonator, such as an AT cut quartz crystal resonator. The nanostructure may be disposed on an electrode surface of the resonator. The plurality of elements may include nanotubes or nanorods, such as ZnO nanorods. The plurality of elements may have at least one of a diameter of about 20 nm to about 60 nm or a length of about 300 nm to about 900 nm. The plurality of elements may be spaced apart by about 20 to about 200 nm. The plurality of elements may have an element density of about 15 to about 25 elements per $\mu m^2$. The resonator may be disposed within a sensor housing, such as a sensor housing that includes a sensor chamber and the plurality of elements may extend into the sensor chamber. The sensor may include an impedance analyzer configured to measure the dissipation of the resonator. The impedance analyzer may include a dedicated circuit disposed within the sensor. An infrared radiation source may be included in the sensor and be configured to irradiate the media to be sensed. The infrared radiation source may include an infrared diode. The sensor may include a heater element configured to increase the temperature of the media to be sensed. The sensor may include a humidity source configured to increase the relative humidity of the media to be sensed. The sensor may include an additive gas source configured to increase the amount of an additive gas in the media to be sensed. The sensor may include a power source. The sensor may be configured to drive the resonator at a variety of driving amplitudes or frequencies or across a range of driving amplitudes or frequencies.

Another exemplary embodiment relates to a method of operating a sensor including driving a resonator of the sensor at a driving amplitude and frequency such that a nanostructure on a surface of the resonator moves through a media to be sensed, measuring a dissipation response of the resonator, and determining the presence of a component in the media to be sensed based on the measured dissipation response. The driving amplitude may be 1 mV to 50 mV. The method may include heating the media to be sensed to a predetermined temperature before measuring the dissipation response of the resonator. The method may include increasing the humidity of the media to be sensed before measuring the dissipation response of the resonator. The method may include increasing the content of an additive gas in the media to be sensed before measuring the dissipation response of the resonator. The method may include irradiating the media to be sensed with infrared energy. Determining the presence of a component in the media to be sensed may include comparing peaks of the measured dissipation response to known dissipation spectra. Driving the resonator may include driving the resonator through a driving amplitude range of 1 mV to 50 mV.

DETAILED DESCRIPTION

According to an exemplary embodiment, a sensor includes a single resonator with a nano-structured surface.

The sensor exhibits improved sensitivity. More precisely, the sensor exhibits an increase in sensitivity up to about 2 orders of magnitude as compared to a single resonator without a nano-structure surface. The sensor operates by measuring and estimating the fluid friction per oscillation cycle, operating in normal conditions without vacuum (e.g., in air or other ambient gas) at room temperature. The sensor can provide measurement data at a speed that is orders of magnitude faster than pre-existing resonance-based methods, as it is based on measurements from a few cycles only. The dissipation-based sensor may be utilized in a broad range of fast, inexpensive, hand-held measuring devices. Additionally, the sensor is capable of operating at standard temperature and pressure.

The structure of the sensor is configured to detect changes in the dissipation behavior of the resonator. The characteristics of the media to be sensed impact the dissipation behavior of the sensor as a result of interaction with the nanostructure. Changes in the characteristics of the media, such as viscosity, are produced by changes in the composition of the media. In this manner, the dissipation behavior of the sensor may be employed to indicate the composition of the media, and changes thereof.

The sensor may include a resonator with flexible nanostructures on a surface of the resonator interacting with the fluid media. The sensor may be responsive to adsorbed particles, changes in fluid medium properties and/or molecular adsorption. Compared with a single resonator device, the inventive sensor is substantially more efficient in the measurement and exploitation of additional dissipation by the choice of the parameter regime and its variation.

The resonator may be any appropriate resonator. For example, the resonator may be a custom designed resonator or an off-the-shelf resonator. According to one embodiment, a standard AT cut quartz crystal (QC) resonator, with the resonator electrode surfaces oriented such that they may contact the media when the resonator resonates, may be employed. The resonator electrodes may be gold electrodes according to one exemplary embodiment, although other materials may be used according to other exemplary embodiments.

Figure 1:
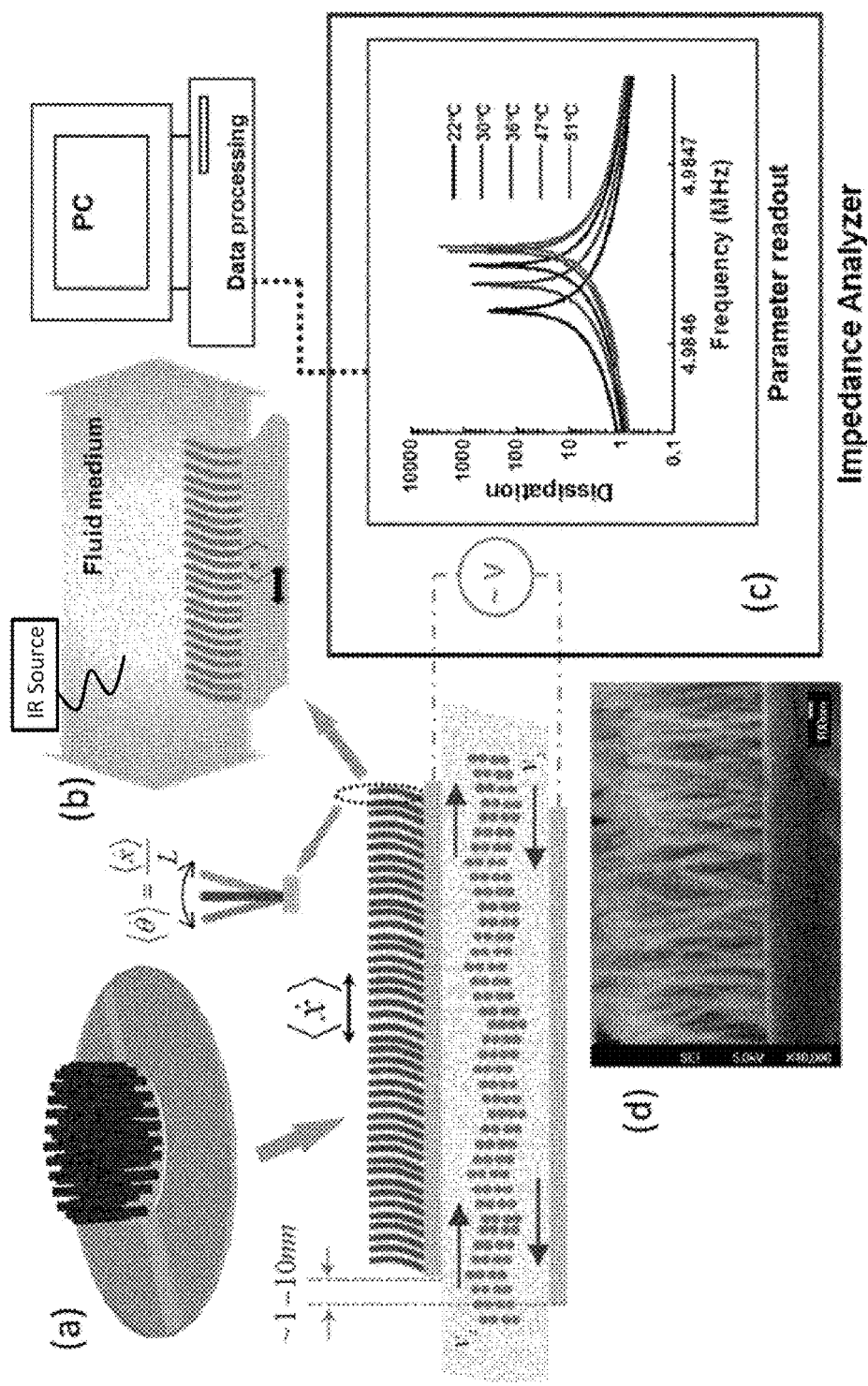
FIGS. 1A-1D depict a schematic representation of a nanostructure disposed on a surface of a resonator; a schematic representation of the nanostructure disposed in a fluid medium; a schematic representation of an experimental apparatus; and an image of the nanostructure disposed on the surface of the resonator, respectively.

The nanostructure is disposed on a surface of the resonator such that the elements of the nanostructure move through the media when the resonator resonates, as shown in FIG. 1B. The nanostructure may include a plurality of elements formed from any suitable material(s), and extending in a direction substantially orthogonal to the surface of the resonator on which they are disposed, as shown in FIG. 1A. The nanostructure may include a plurality of nanotubes or nanorods. According to one embodiment, the nanostructure may include a plurality of ZnO nanorods grown on one of the electrode surfaces of the resonator, as shown in FIG. 1D.

The elements of the nanostructure may have any suitable dimensions. According to one embodiment, the elements of the nanostructure may have a diameter in the range of about 20 nm to about 60 nm, such as a diameter in the range of about 30 nm to about 50 nm. The elements of the nanostructure may have a length in the range of about 300 nm to about 900 nm, such as a length in the range of about 500 nm to about 700 nm. According to another embodiment, the elements of the nanostructure may have a diameter similar to the diameter of a target particulate material to be sensed.

The nanostructure may have any suitable element density. According to one embodiment, the element density of the nanostructure should be such that the distance between the elements is similar to the molecular mean free path in the media. For example, in the case where the sensor will be utilized with an air-based media in normal temperature and pressure conditions, the spacing between the elements of the nanostructure may be between about 20 nm and about 200 nm, such as between about 50 nm and about 100 nm, or about 60 nm and about 70 nm. The element density of the elements on the nanostructure may be in the range of about 15 to about 25 elements per $\mu m^2$, such as about 18±2 elements per $\mu m^2$, providing an area coverage of about 8% per $\mu m^2$ of projected surface area. If the element density of the nanostructure is too low, the impact of the nanostructure on the dissipation of the resonator is undesirably reduced, and if the element density is too high the media is prevented from entering the space between the elements of the nanostructure and the sensor does not effectively detect changes in the media.

Figure 2A:
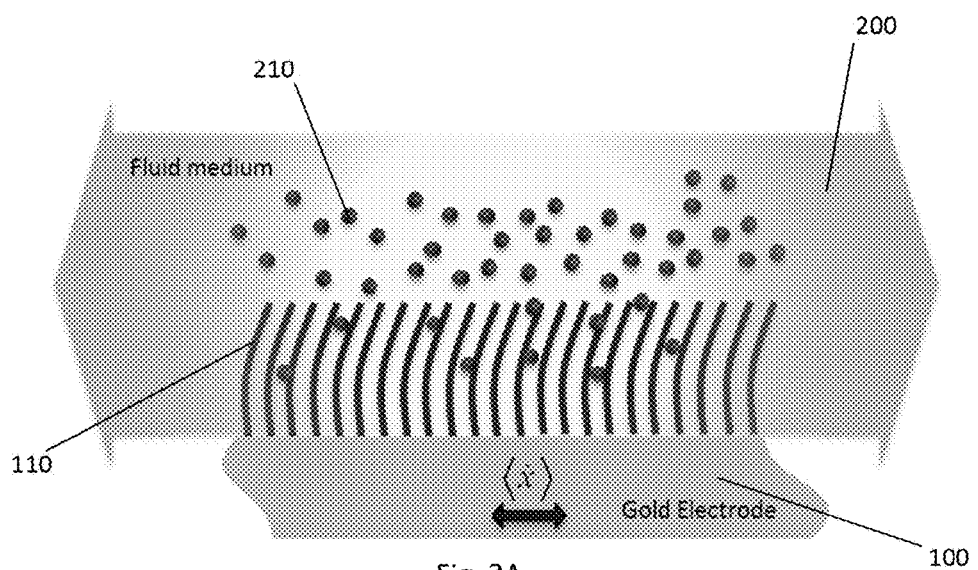
FIGS. 2A and 2B depict schematic representations of the interaction of the elements of a nanostructure with a fluid media including particulates.
Figure 2B:
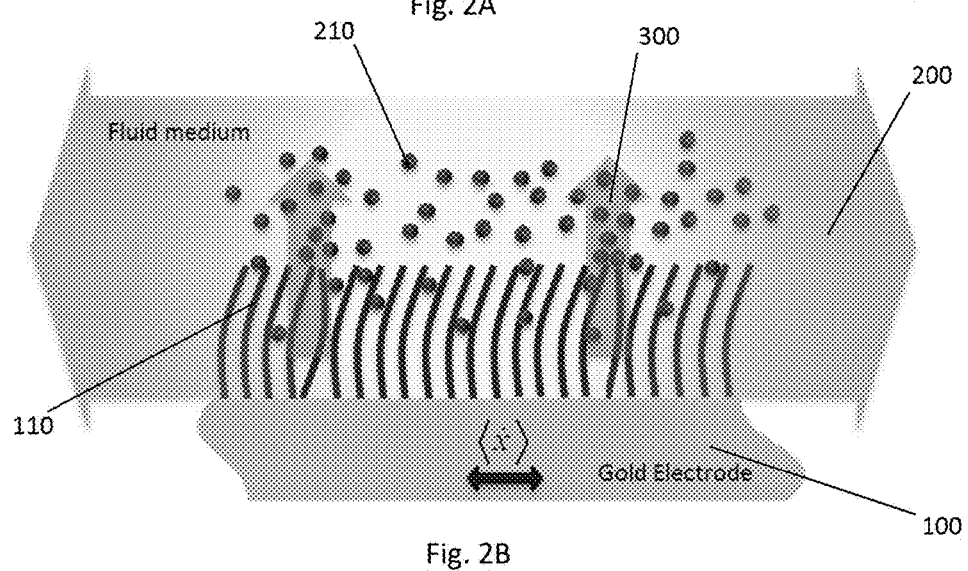

A schematic representation of the dissipation of energy from the resonator in the presence of a particulate containing fluid media is depicted in FIGS. 2A and 2B. The particulates 210 in the fluid media 200 interact with the elements 110 of the nanostructure disposed on the electrode 100 of the resonator in a manner that disrupts the motion of the elements through the fluid media 200. As shown in FIG. 2B, the disruption of the motion of the elements 110 of the nanostructure on interaction with the particulates 210 produces a spontaneous out-of-phase motion of the elements and an increase in dissipation by transferring additional energy 300 to the fluid media 200. In this manner, the presence of particulates in the fluid media may be detected.

The nanostructure may be produced on the resonator surface by any appropriate process. The nanostructure elements may be grown in-situ on the resonator surface. According to one embodiment, a seed layer for growth of the elements may be disposed over the surface of the resonator before the growth of the elements. The area of the resonator surface covered with the seed layer may be controlled with the use of a mask, such that the area of the seed layer corresponds to the area to be covered with the grown elements. Alternatively, pre-formed nanostructure elements may be disposed over the resonator surface.

The resonator may be provided in a sensor housing, such that the elements of the nanostructure are exposed to a media in a sensor chamber formed in the sensor housing. The sensor chamber may be in fluid communication with the atmosphere, and may be configured to facilitate the rapid turnover of the media in the sensor chamber. The sensor housing may additionally include circuitry configured to measure the dissipation of the resonator. Alternatively, the sensory housing may include interconnects that are configured to attach the sensor to a power source, an external apparatus configured to measure a dissipation of the resonator, or both. A handheld sensor device may be provided in which the sensor housing additionally includes a power source, such as a battery or fuel cell.

The resonator may be connected to an impedance analyzer that is configured to measure the dissipation of the resonator. The impedance analyzer may be a commercially available impedance analyzer. Alternatively, the impedance analyzer may be a custom designed impedance analyzer, such as an impedance analyzer configured to be disposed in the sensor housing or to have size compatible with portability. The data produced by the impedance analyzer may indicate a change in the composition of the media, the concentration of individual components of the media, or the presence of a new component in the media. The data produced by the impedance analyzer may include a peak dissipation frequency, a shape of the dissipation curve as a function of frequency, a peak dissipation, or combinations thereof. The dissipation data may be processed by a computer that receives output from the impedance analyzer.

The media in the sensor chamber may be a mixture of gases or vapors. For example, the media may have a composition substantially similar to air, with the dissipation characteristics of the resonator changing as the composition of the media changes. According to one embodiment, the media may be substantially similar to air with the sensor configured to detect changes in the medium, such as the inclusion of pollutant vapors. Alternatively, the media may include particulates in addition to the gases or vapors. The sensor may be capable of detecting the presence of particulates in the media without the particulates attaching to the elements of the nanostructure.

The sensitivity of the present sensor with respect to temperature allows the possibility of selectivity of the dissipation-based sensing. According to one embodiment, a variable-wavelength IR diode may be provided to irradiate the media in the sensor chamber. A scan through the frequency range in the IR spectrum results in temperature increases at the IR absorption wavelength of the media, yielding higher dissipation. The dissipation may be measured on the order of a few milliseconds with a 5 KHz BW sweep for a sweep time of 30-45 seconds and the turnover of air in the chamber takes on the order of a fraction of a second, allowing a scan in an IR range of 100 frequencies to be completed in between about 1 and about 10 seconds. The dissipation exhibits high peaks whenever there are peaks in the corresponding IR absorption spectrum of the media. Thus, the sensor device may differentiate between different media components, as long as the media components have sufficiently different IR absorption spectra.

The sensor may be employed to monitor changes in the composition of the medium, and thereby the environment, for example at normal pressure and temperature. The sensor may be utilized to detect the presence of undesired contaminants or pollutants in the environment. According to one embodiment, the contaminants or pollutants may include chemical species, smoke particulates, or viruses. For example, the sensor may be employed to detect the release of chemicals associated with oil, gas, or mineral recovery or processing. The sensor may also be employed to detect forest fires by detecting carbon particles associated with smoke, or to detect fine stone or mineral particulates. Alternatively, the sensor may be employed in an industrial environment to detect undesired chemical release. The sensor may also have anti-terrorism applications in the detection of chemical or biological agents. The sensor may be employed in health applications by providing an analysis of the chemical components in the fluids or gases produced by the body. According to one embodiment, the sensor may be configured to detect the presence of a specific media component. The detection of viruses with the sensor may be enabled by IR irradiation as discussed above.

The sensor may be based on the mechanical properties and response of the nanostructure. The amplitude of the motion of the nanostructure may affect the dissipation of the sensor. Dissipation peaks at a specific driven amplitude may be characteristic of particular molecules or other species interacting with the nanostructure. The amplitude at which the nanostructure is driven may be optimized to achieve a particular value which produces a drastic increase in dissipation, while the driven frequency is kept constant or varied throughout a predetermined range. This selective increase in dissipation may increase the selectivity of the sensor for a desired molecule that exhibits characteristic dissipation at the selected amplitude. Alternatively, the amplitude at which the nanostructure is driven may be scanned through a predetermined range, producing several dissipation peaks, while the driven frequency is kept constant or varied throughout a predetermined range. The characteristic dissipation peaks as a function of driven amplitude may be employed to identify specific molecules in the media. Other features of the dissipation peaks may also be utilized to increase the specificity and selectivity of the sensor, such as the shape of the peaks and the area under the peaks. The sensor may thus be utilized to produce a mechanical spectrum characteristic of the media interacting with the sensor, based on the dissipation behavior of the sensor as a function of driven amplitude. A similar mechanical spectrum may also be produced for dissipation as a function of driven phase. Without wishing to be bound by any particular theory, the dependence of the dissipation on the driven amplitude of the nanostructure may be due at least in part to the molecules interacting with the nanostructure exhibiting different resonant frequencies. The range of the driven amplitude, when converted to voltages, may be on the order of millivolts (mV), such as 1 mV to 50 mV or 5 mV to 50 mV.

The operation of the sensor is based on the effect of the interaction of the media and the nanostructure on the dissipation characteristics of the resonator. The interaction of the nanostructure and the media may be theoretically modeled, based on the characteristics of the media and the nanostructure.

The current understanding of fluid friction for a small (e.g., micron size) vibrating string is based on the work of Stokes, in which the motion of the string is governed by the balance of inertia, elastic and drive forces, and the viscous drag forces inhibiting the motion. The ratio of inertial to viscous forces is defined as the Reynolds number $$Re = \frac{\rho U L}{\eta},$$

which becomes the parameter of dynamic modulation, where U and L are the characteristic velocity and length of the resonator, respectively, and $\rho$ and $\eta$ are the density and dynamic viscosity of the ambient fluid, respectively. Near or at resonance, the inertial and stiffness forces balance each other such that the kinetic energy and potential energy match, rendering the system behavior predominately a function of the ratio of driving forces to damping. Therein lies the significance of reducing friction to obtain a narrowband resonance. For high vacuum conditions, the viscous effects are more complex, as the ambient media becomes an extremely rarified gas, and the internal dissipation in the resonator plays a dominant role in the dynamic response modulation of the resonator. Contrary to previous efforts, the sensor of the present invention is based on enhancing the dissipation of a single resonator in a way that it makes the energy loss per cycle detectable and a useful tool for sensing. To enhance the dissipation of the resonator, the physical system, and correspondingly, the Reynolds number, is changed by augmenting the surface of the resonator with flexible nanostructures. The flexible nanostructures may exhibit significantly different length and time scale response compared to the resonator.

The sensor may utilize any appropriate resonator with flexible nanostructures on a surface of the resonator that is configured to interact with the fluid media. The sensor may be responsive to adsorbed particles, changes in fluid medium properties, and/or molecular adsorption. Compared with a single-resonator device that does not include a nanostructure on the surface thereof, the inventive sensor is substantially more efficient in the measurement and exploitation of additional dissipation based on a selected parameter regime and its variation.

The sensitivity of the present sensor with respect to temperature allows the additional possibility of selectivity of the dissipation-based sensing. Different compositions of ambient air produce different viscosities as a function of temperature. A change in the temperature of the fluid, or other external parameter of the fluid, produces a different viscosity change for different compositions of the ambient air supplied to the sensor. According to one embodiment, an external heating element may be employed to produce a predefined change in the temperature of the ambient air taken into the sensor, and viscosity change produced by the change in temperature may indicate the composition of the ambient air supplied to the sensor. According to another embodiment, other properties of the ambient air supplied to the sensor may be changed in a predefined manner, and the resulting viscosity change indicates the composition of the ambient air. For example, the composition of the air supplied to the sensor may be modified. Modifications of the air supplied to the sensor may include introducing additional humidity or mixing the ambient air with a controlled quantity of gas, such as nitrogen, from a gas supply. The changes in the ambient air properties employed may be any appropriate change that produces a change in viscosity.

According to another embodiment, a variable-wavelength IR diode irradiating the air in the chamber may be provided. A scan through the frequency range in the IR spectrum will result in temperature increases at the IR absorption wavelength of the media, yielding higher dissipation. The dissipation may be measured on the order of a few milliseconds with a 5 KHz BW sweep for a sweep time of 30-45 seconds, and the turnover of air in the chamber takes on the order of a fraction of a second, allowing a scan in an IR range of 100 frequencies to be completed in between about 1 and about 10 seconds. The dissipation will yield high peaks whenever there are peaks in the corresponding IR absorption spectrum of the media. Thus, the sensor device may differentiate between different media components, when the media components have sufficiently different IR absorption spectra.

Considering, for simplicity, a pendulum-like motion of the slender rod, the Reynolds number may be defined as:

$$Re = \frac{\rho_{fl} d^2}{4\eta}\left(\frac{\sqrt{\langle \dot{x}^2 \rangle}}{L}\right) = \frac{\rho_{fl} \langle \dot{\theta} \rangle d^2}{4\eta} = \frac{\rho_{fl} \omega_{rod} d^2}{4\eta} \left[\text{where, } \omega_{rod} = \langle \dot{\theta} \rangle = \frac{\sqrt{\langle \dot{x}^2 \rangle}}{L}\right],$$

with an inertial factor contribution impacted by the density of the fluid $\rho_{fl}$, the diameter of the slender rod d and its length L, while a viscous factor contribution is influenced by the dynamic viscosity of the fluid $\eta$ and the linear velocity $\sqrt{\langle \dot{x}^2 \rangle}$ with which the fluid in contact with the slender rod is dragged along, and $\langle \dot{\theta} \rangle = \omega_{rod}$ being the angular velocity of the slender rod. A more complex theory based on flexible beam dynamics can be constructed, producing essentially the same order of magnitudes up to a constant pre-factor. It follows that the angular velocity of the rod is modulated by the frequency of the platform drive $\Omega$ as $$\omega_{rod} = \frac{\Omega \times x}{L};$$

which is evidently much smaller than the rod's resonant frequency $\omega_{res} \cong 10^8$ Hz, with L essentially governing the boundary layer thickness of fluid $$\delta = \left(\frac{2\eta f_\omega}{\rho_{fl}\omega_{rod}}\right)^{1/2},$$

and $f_\omega$ being the dimensionless frequency parameter as defined later. For a rod where the characteristic length scale is of the order of tens to hundreds of nanometers, Re significantly reduces to values of the order of $\sim 10^{-5}$–$10^{-7}$ as a function of the dimensionless frequency parameter $$f_\omega = \frac{\omega_{rod}}{\Omega} = \frac{\dot{x}}{\Omega L} = \frac{x}{L};$$

with x making the motion dominated by viscous drag. At normal temperature and pressure, determining the regime of flow from the order of magnitude of the Reynolds number is essential in calculating the fluid forces on the rods. For similar boundary layer thicknesses, Re typically approaches a value on the order of between approximately 1 and 10 for a bare vibrating platform and a rod at micron scale, with the diameter being the characteristic length, signifying inertial factor dominance. At the nanoscale, however, fluid damping dominates over fluid inertia which indicates dissipation dominance at the operational regime of very low Reynolds number. For a dense forest of such slender rods vibrating together, and considering linear coupling, dissipation may be considered as a function of the number density of fabricated nanorods N and their geometry (characterization results shown later), which further allows the estimation of the fluid damping coefficient $\gamma$ and fluid added mass $M_{fl}$. Consequently, the dimensionless dissipation factor expressed as a ratio of the dissipated to stored energy per cycle for the bigger resonator can be represented as $$D = \frac{E_{diss}}{E_{stored}} = \frac{\int_0^T \vec{F}_{visc} \cdot \vec{x} dt}{E_{kinetic} + E_{potential}} = \frac{\int_0^T \gamma \dot{x}^2 dt}{\frac{1}{2T}\int_0^T (\dot{x}^2 + \omega_0^2 x^2) dt} = \frac{\gamma \int_0^T \omega_0^2 x^2 dt}{\frac{1}{T}\int_0^T \omega_0^2 x^2 dt} = \frac{\gamma}{f},$$

where T is the time period of oscillation and $\omega_0 = 2\pi f$.

There are two possible ways for the Reynolds number to change. One way is to change the medium, for example by saturating the air with the vapor of a media, or, alternatively, replacing the air altogether by another gas. In the case of complete replacement, the effective variation in Re with the medium follows $$\frac{Re_{air}}{Re_{vapor}} = \left(\frac{\rho_{air}}{\rho_{vapor}}\right) / \left(\frac{\eta_{air}}{\eta_{vapor}}\right) = (v_{vapor}/v_{air}),$$

where the dynamic viscosity $\eta$ variation may be estimated. For a complex vapor mixture of air and volatile chemicals, air molecules of the fluid medium around the nanorods are replaced by molecules of the vapor depending upon its number density and molar mass, which in turn results in an effective change in the Reynolds number.

The effect of ambient fluid friction manifested through Reynolds number Re has been typically modeled as a complex-valued hydrodynamic drag force, where the analysis of the real and imaginary parts of the force provides information on the added fluid mass displaced by the resonating element and the damping coefficient caused by the fluid, respectively. However, such a formulation is restricted to the continuum regime alone, and is only valid for a free vibrating string in an infinite fluid. A similar approach has previously been employed to study the behavior of microorganisms at very low Reynolds Number regimes. The linear combination of a finitely large number of such slender rods collectively adding to dissipation is a naive approach theoretically. Estimation with respect to fixed nanorod geometry, number density and operation regime typically accounted for a variation in dissipation factor by 1% for an effective Reynolds number variation of the order of 1%. Previous work relating the changes in dissipation as a function of vapor properties for a bare crystal also estimated similar variations. However, the present experimental results clearly show a dissipation variation on the order of 100% for an effective Revariation of 1%. Thus, the previous theoretical considerations are not entirely compatible with the present system.

As it follows, the system cannot be looked upon as mutual addition of individual viscous forces of N rods, where the viscous friction computed with Stokes formulation considers each rod to be independent of the other in an infinite fluid medium. The system is a global ensemble of coupled slow moving oscillators, where the mutual phase relations between the nearest neighbors govern the overall viscous friction. Entrainment of random ordered vibrating structures produce an in-phase motion coupling of the nearest neighbors, achieving a dynamic ordered/stable state. Such an entrained system thus becomes less prone to damping effects, since the forced steady state brought about by the long range viscous forces makes the system energetically more favorable.

It is only when random out of phase motion is considered that the fluid-nanostructure interaction generates a higher velocity gradient as a function of effective volume change between the two nearest neighbor rods following $$\frac{dV}{dt} = U \cdot S,$$

where U is the velocity and S the cross sectional area. This accounts for localized energy generation of the cell involving out-of phase structures $\Delta E = V \cdot \rho \cdot U^2/2$, which results from dissipation in the system. However, for the typical dimension of the nanorods and vibrational amplitude a of the order of $\sim 1$ nm, the mean free path of the molecules is $1_* \gg a$, making the fluid a non-continuous fluid relative to the rods in motion in between the nanorods. In effect, when a rod pushes a fluid by a, it actually pushes fluid by $a+1_* = a_{eff}$. Hence it follows that:

$$\frac{dV}{dt} = L \cdot d \cdot a_{eff} \cdot f \cong Ld^2 f$$

with d being the distance between rods and f being the frequency. It then follows that:

$$\Delta E = \tfrac{1}{2}\rho L^3 d^2 f^2.$$

Possibilities for the dissipation include one given by the friction of the rods with the fluid molecules due to normal impact and another due to the friction between the fluid molecules. The second possibility is responsible for the regular lubrication viscous friction in narrow channels. However, in the present framework the distance between the rods is of the same order, or smaller, than the mean-free path of the molecules, rendering the impacts between the molecules less likely than the impacts between the fluid molecules and the rods. Thus, the lubrication-type friction can be neglected, leaving the friction encountered by the rods themselves to account for the dissipation. In the case of rod motion, even in rarified gas, the regular formulas of the rod friction can be employed with appropriate corrections. Thus, the dissipation of the rod due to viscous forces that would cause a change of state of the rod is $\Delta W = 2\pi v C \rho v^2 L/f$, with v being the velocity of the rods. The probability p of the random generation of the off-phase state, expected to be described by Boltzmann statistics as derived from Gibbs measure, is proportional to:

$$p \propto \exp\left(-\frac{\Delta E}{\Delta W}\right),$$

up to the normalizing factor that is expected to change slowly with media parameters. Since the dissipation in the in-phase states is much lower than the out-of-phase states, the dissipation is proportional to $$D = \Delta W \cdot \exp\left(-\frac{\Delta E}{\Delta W}\right).$$

A small change in viscosity from $v \rightarrow (v+\Delta v)$ leads to the change of the factor $$\frac{1}{v}$$

in exponent as $$\Delta\left(\frac{1}{v}\right) = -\frac{\Delta v}{v^2},$$
$$\frac{\Delta v}{v} \ll 1.$$

Thus, under a change of viscosity from $v \rightarrow (v+\Delta v)$, the argument of exponent changes as:

$$-\frac{\Delta E}{\Delta W} = K\left(\frac{\Delta v}{v}\right),$$

where K is a dimensionless constant and related to the parameters of the resonator as described below.

This results in relative dissipation change caused by the corresponding relative kinematic viscosity change computed as:

$$\frac{D}{D_0} = \exp\left(\frac{1}{4\pi}\frac{L^2 f}{Cv}\left(\frac{d}{a}\right)^2 \cdot \frac{\Delta v}{v}\right) = \exp\left(K \cdot \frac{\Delta v}{v}\right).$$

Typical order of magnitudes for the system in question gives a factor of K=10, which produces a change in dissipation on the order of 2 for even a 1% change in kinematic viscosity. This theoretical result is corroborated by experimental results. In effect, D increases for increasing v.

Calculations with respect to dry air for variations with passing water vapor, Ethyl Alcohol (EOH) and petroleum ether (PE) change the effective kinematic viscosity within the same range as that conducted for temperature measurements which result in similar dissipation variations.

Another way the dissipation can change for a given ambient media is by simply changing the geometric scale of the nanorods due to adsorption of the particles effecting a change in resonator volume or the viscous layer thickness. In principle, the sensing methodology is applicable to detection of any particles having a geometric size comparable to the characteristic dimension of the nanorod independent of their masses. For example, the sensor may be employed to detect particles in smoke produced as a result of combustion, such as that produced by forest fires.

All the discussions above become relevant when considering the electrical resonance model of a quartz crystal microbalance (QCM) resonator platform. The added dissipation is reflected as an added complex impedance variation where the Resistance change is proportional to viscous damping. The added fluid mass is reflected as a variation in the Inductance variation, changing the stored energy per cycle of its oscillation. The ratio of the dissipated to stored energy per cycle is reflected as a dimensionless Dissipation-factor variation, $$D = \frac{R_s}{X_s} = \frac{R_s}{\omega L_s},$$

which may be obtained through complex impedance analysis using an Impedance analyzer. The obtained Dissipation factor (D) is a measure of the loss-rate of energy of a mode of oscillation in a dissipative system. It is expressed as the ratio of the resistive power loss in the equivalent series resistance ($R_S$) to that stored in the series reactance ($X_S$), which in the present case of inductive reactance, $X_S = X_L = \omega L_S$, where $L_S$ is the series inductance of the system.

Although the present disclosure contemplates a wide variety of dissipation-based sensors and methods of making the same, the following example is provided by way of illustration, and are not intended as limiting with respect to the present disclosure and the scope of the inventions described herein. Accordingly, it should be understood that other materials and combinations of materials, and methods of making the same, are contemplated by the present disclosure and are intended to be a part hereof.

EXAMPLE

ZnO nanorods were grown on one of the gold electrode surfaces of a standard AT cut quartz crystal (QC) resonator. Zinc nitrate hexahydrate ($Zn(NO_3)_2 \cdot 6H_2O$, 98%), ammonium hydroxide (28 wt % $NH_3$ in water) were purchased from Sigma-Aldrich. A 10 nm-thick ZnO seed layer was sputtered on an electrode of the cut quartz crystal resonator.

The ZnO seed layer was deposited on only one of the electrode surfaces by employing a mask. ZnO nanorods were then grown on the coated quartz crystal resonator by submerging the resonator in a 10 mM $Zn(NO_3)_2 \cdot 6H_2O$ solution and maintaining a pH of the solution of 10.6 by adding ammonia to the solution. After hydrothermal growth of the ZnO nanorods in an oven at 90° C. for 3 h, the crystals were rinsed with de-ionized water and ethanol and dried in a vacuum oven.

Figure 3A:
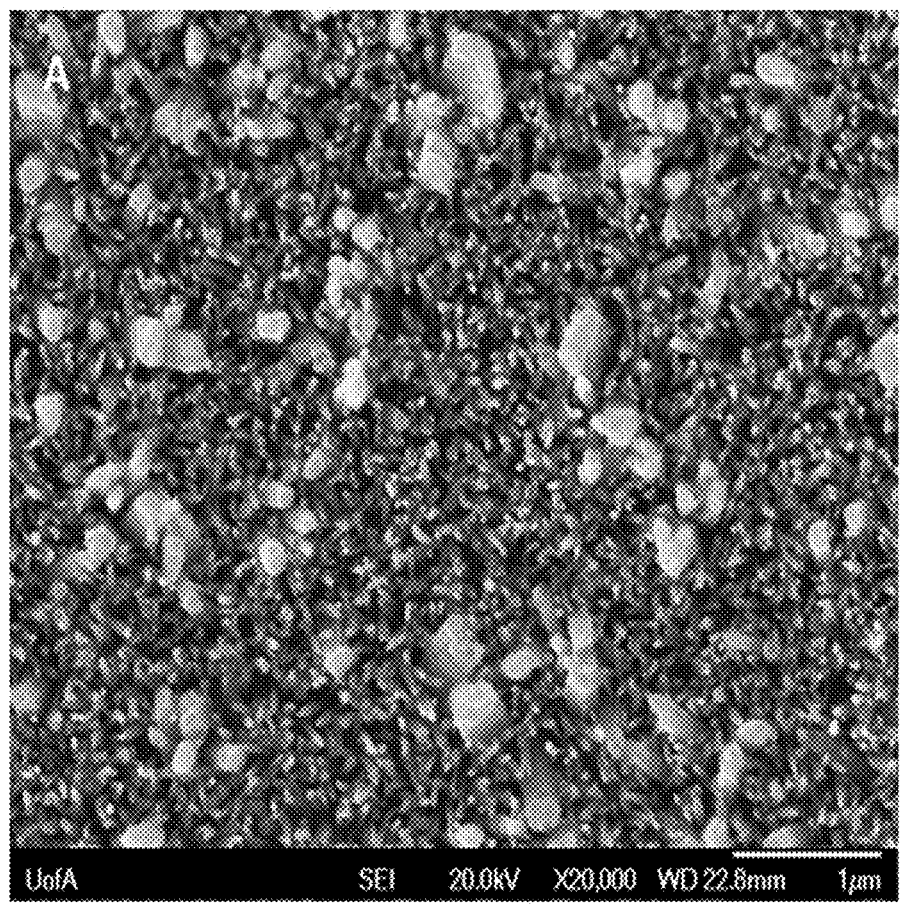
FIGS. 3A, 3B, and 3C depict a field emission scanning electron microscopy image (FE-SEM) image of a top view, a side view, and multiple perspectives of zinc oxide (ZnO) nanorods grown on a 10 nm seed layer of ZnO on an electrode of a resonator, respectively.
Figure 3B:
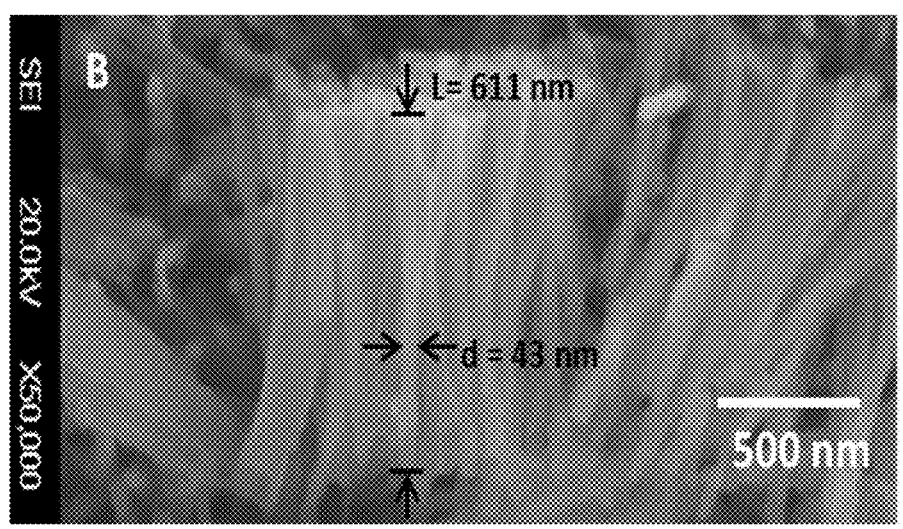
Figure 3C:
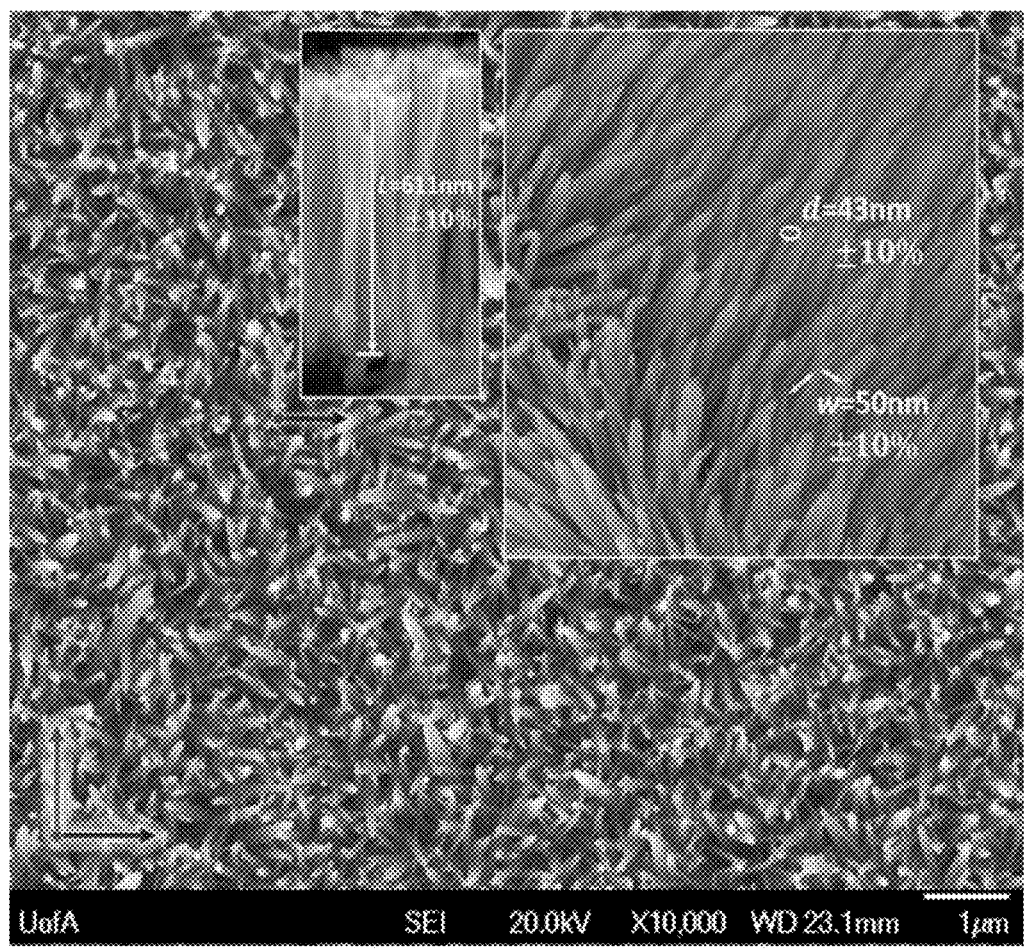

FE-SEM images of the ZnO nanorods are shown in FIGS. 3A, 3B, and 3C. The estimated of length of the ZnO nanorods was 611 nm, while the diameter of the ZnO nanorods was 43 nm as shown in FIG. 3B. The nanorod density measured at different locations was about 18±2 nanorods per 1 $\mu m^2$, providing an area coverage of about 8% per 1 $\mu m^2$ of projected surface area. As shown in FIG. 3C, the spacing between the nanorods was about 50 nm.

The impedance parameters of the resonator were measured using an Agilent 4294A impedance analyzer with a frequency range of 40 Hz to 110 MHz and a nominal impedance accuracy of +/−0.08% at 100 Hz. The impedance analyzer exhibited excellent high Q or D accuracy, enabling reliable analysis of low-loss components. The inherent high dynamic range of the equipment allowed device evaluation under actual operating conditions. A fixed ac test signal level of Vrms ~ 5 mV was employed for all the impedance based dissipation measurements. A schematic representation of the experimental method is illustrated in FIG. 1C.

Figure 4A:
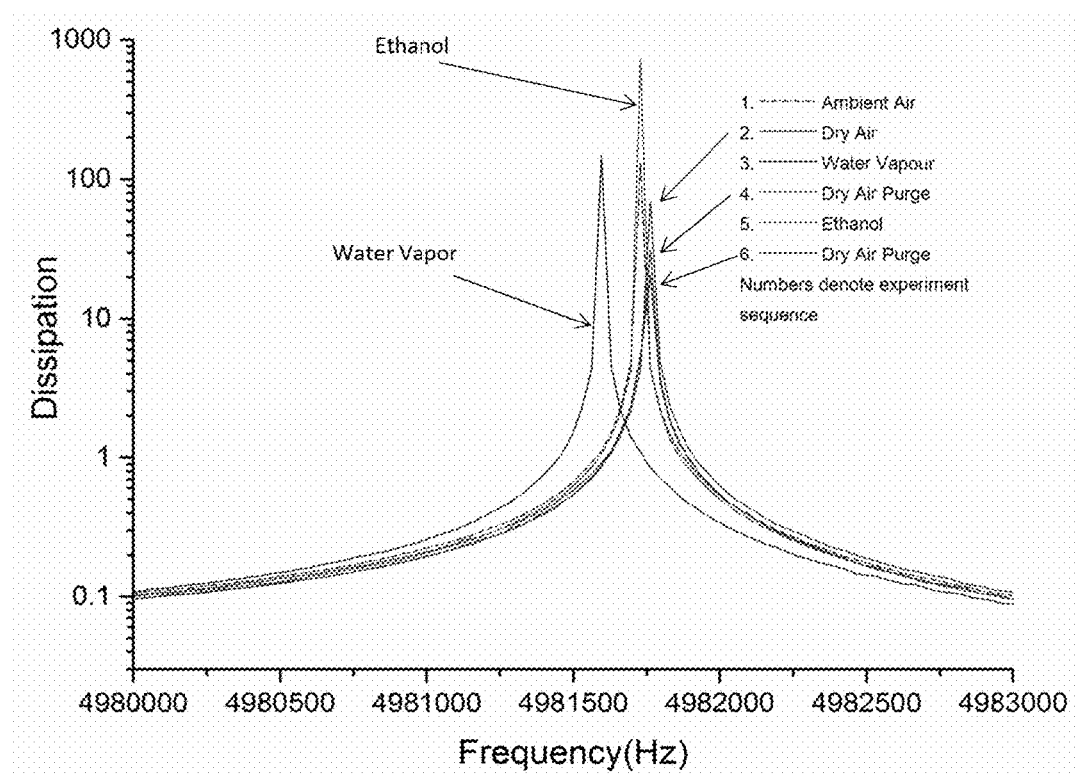
FIGS. 4A, 4B, and 4C depict dissipation as a function of frequency for a variety of different media, with the inset in FIG. 4C depicting the measured dissipation as a fraction of the dissipation for dry air for various media pollutants.
Figure 4B:
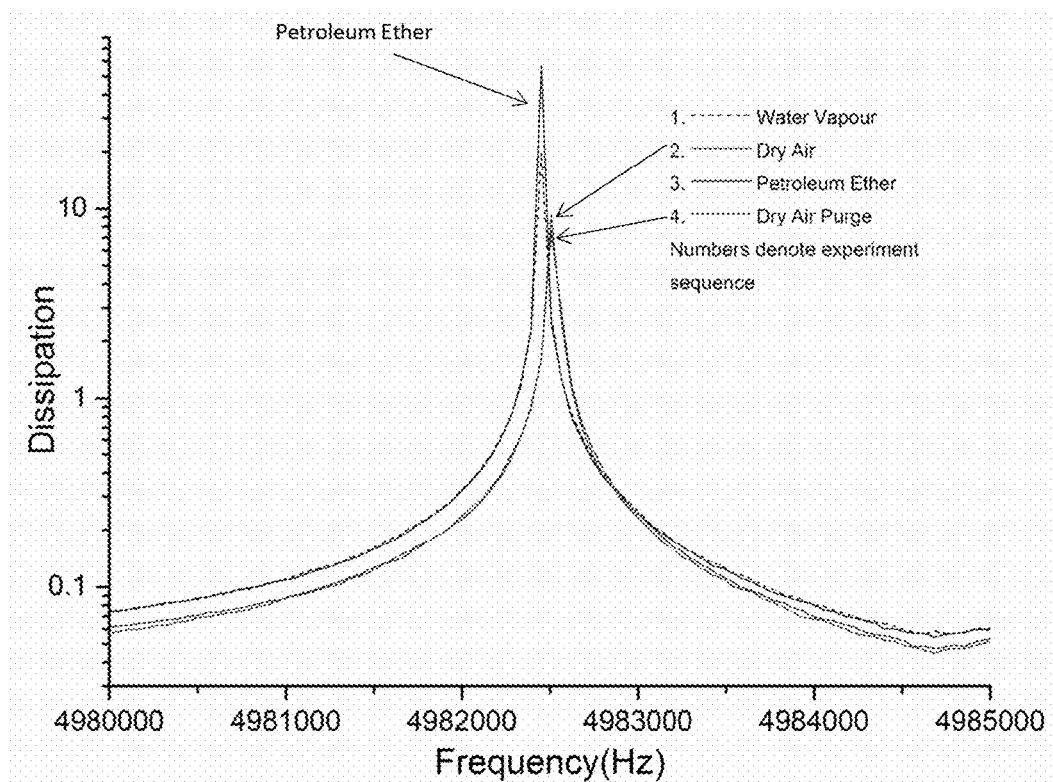
Figure 4C:
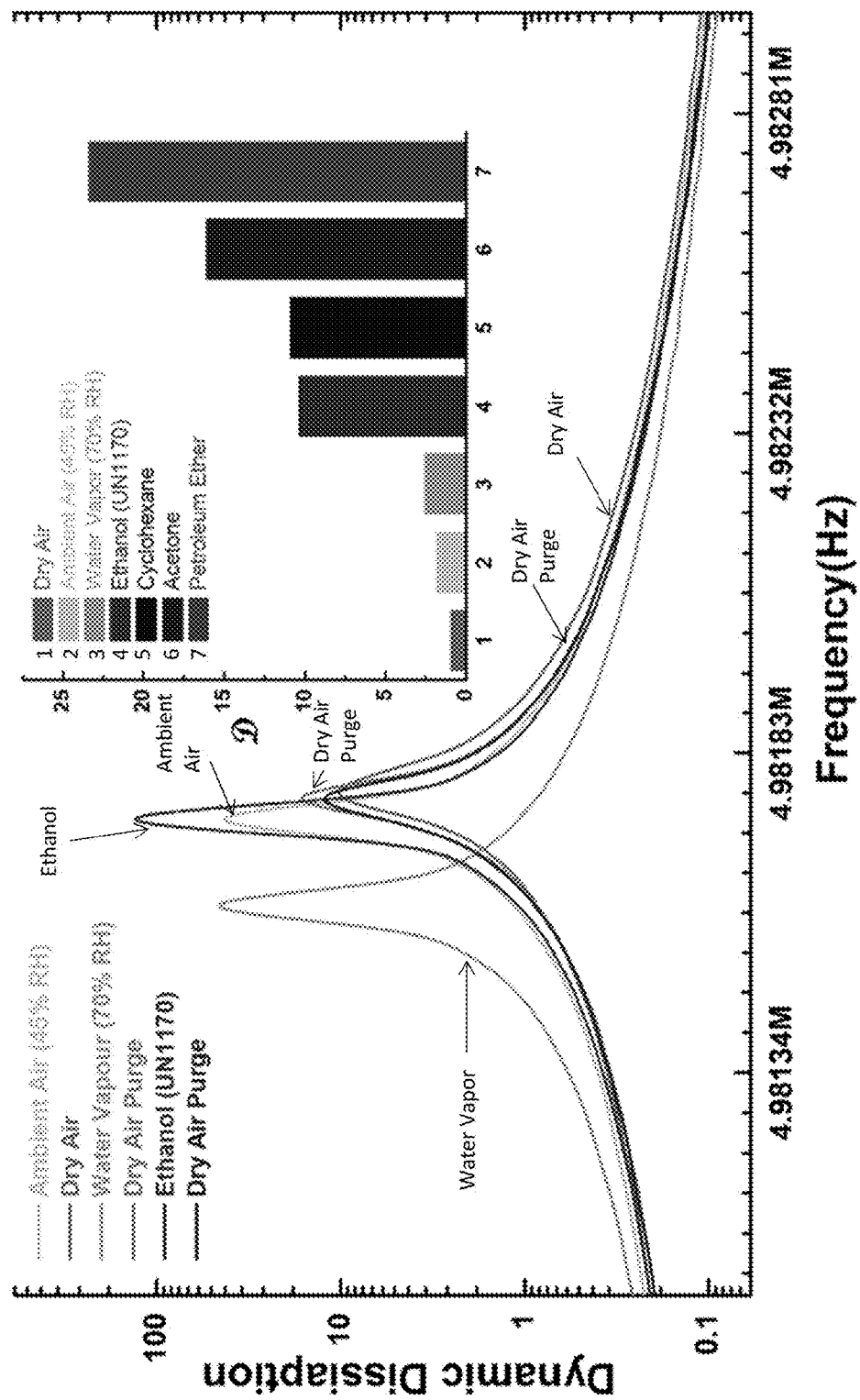
Figure 5A:
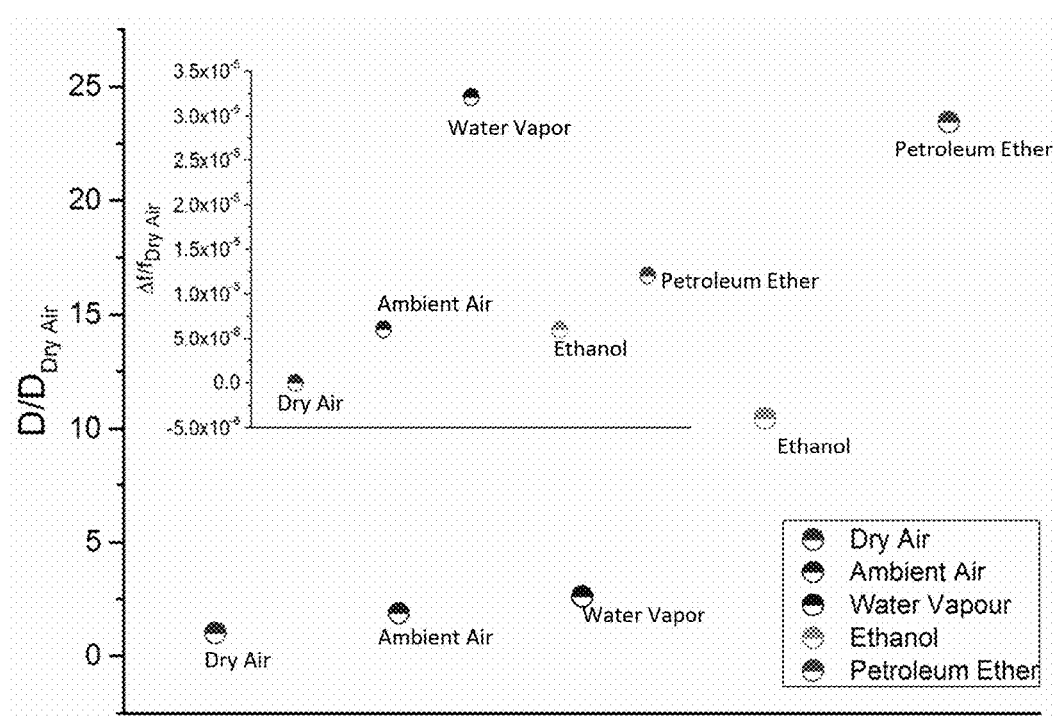
FIGS. 5A and 5B depict the measured dissipation as a fraction of the dissipation for dry air and for various media pollutants, and a change in relative frequency with temperature dependent kinematic viscosity change for dry air at various temperatures and various media pollutants, respectively, with the inset of FIG. 5A depicting a corresponding change in frequency.
Figure 5B:
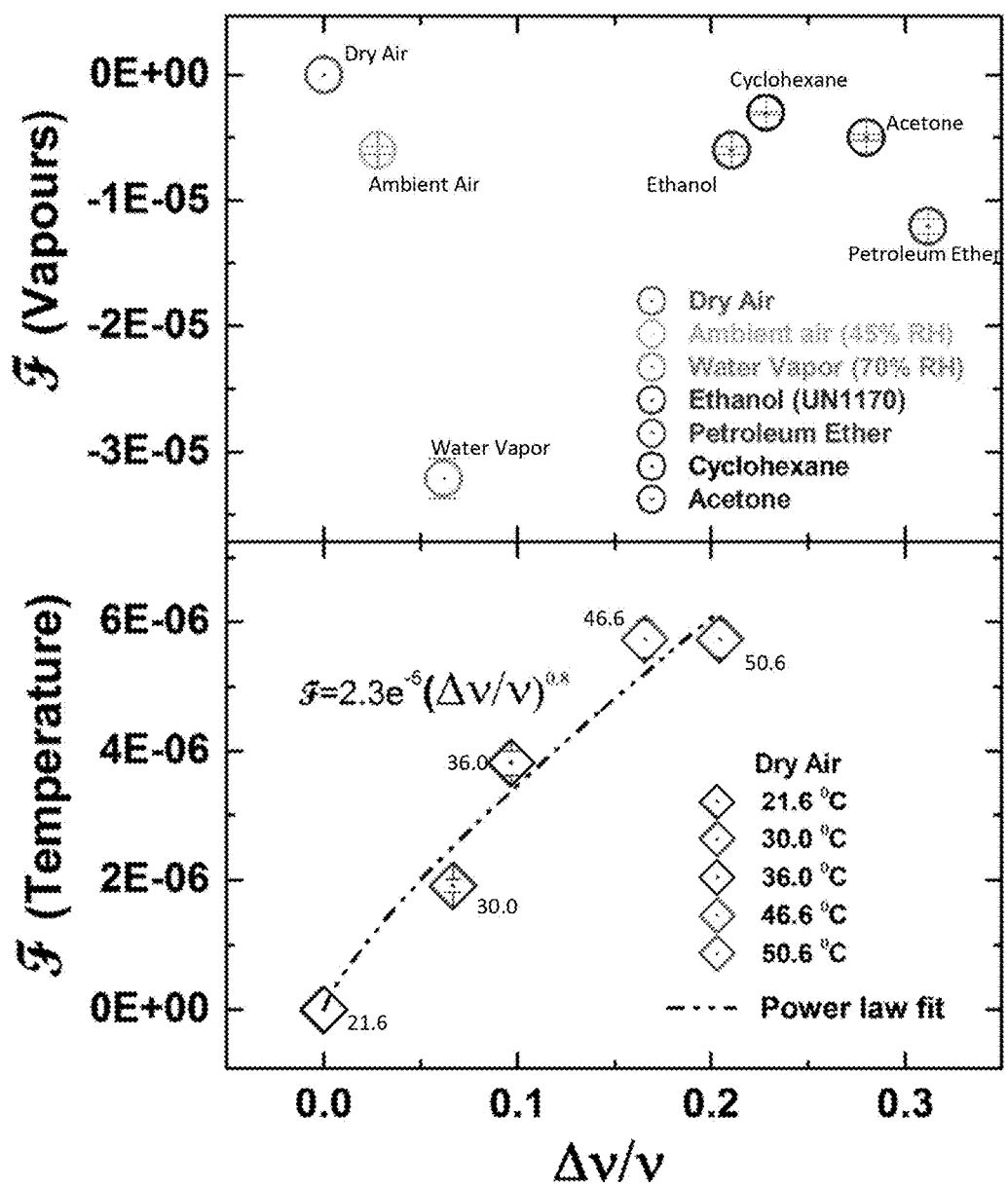

The obtained Dissipation factor (D) is a measure of the loss-rate of energy of a mode of oscillation in a dissipative system. It is expressed as the ratio of the resistive power loss in the equivalent series resistance ($R_S$) to that stored in the series reactance ($X_S$). FIGS. 4A and 4B show examples of the dissipation and frequency shift measurement. In order to demonstrate that the change in dissipation is caused by the change in kinematic viscosity, a series of experiments measuring dissipation of dry air as a function of different media were conducted. The data for different ambient media obtained from FIGS. 4A and 4B are summarized in FIG. 5A, with each data point in FIG. 5A representing the analysis of the data presented in FIGS. 4A and 4B. FIG. 4C shows additional examples of the dissipation and frequency shift measurement for different ambient media, and the inset in FIG. 4C summarizes the data for the different ambient media. The inset in FIG. 5A shows the corresponding change of the frequency, and demonstrates that the frequency change, while noticeable, is not conducive to precise measurements, as the change in frequency does not accurately differentiate between different media.

Figure 6A:
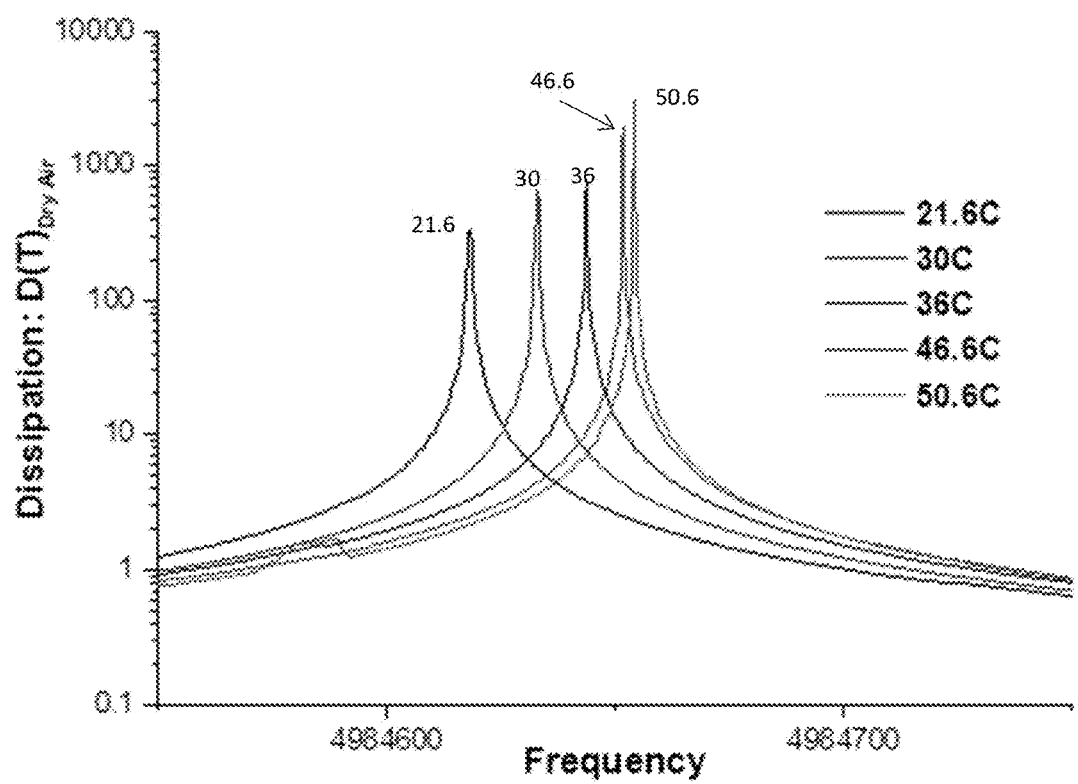
FIGS. 6A and 6B depict dissipation as a function of frequency for a variety of ambient dry air temperatures, with the inset in FIG. 6B depicting the dissipation response of dry air as a function of temperature.
Figure 6B:
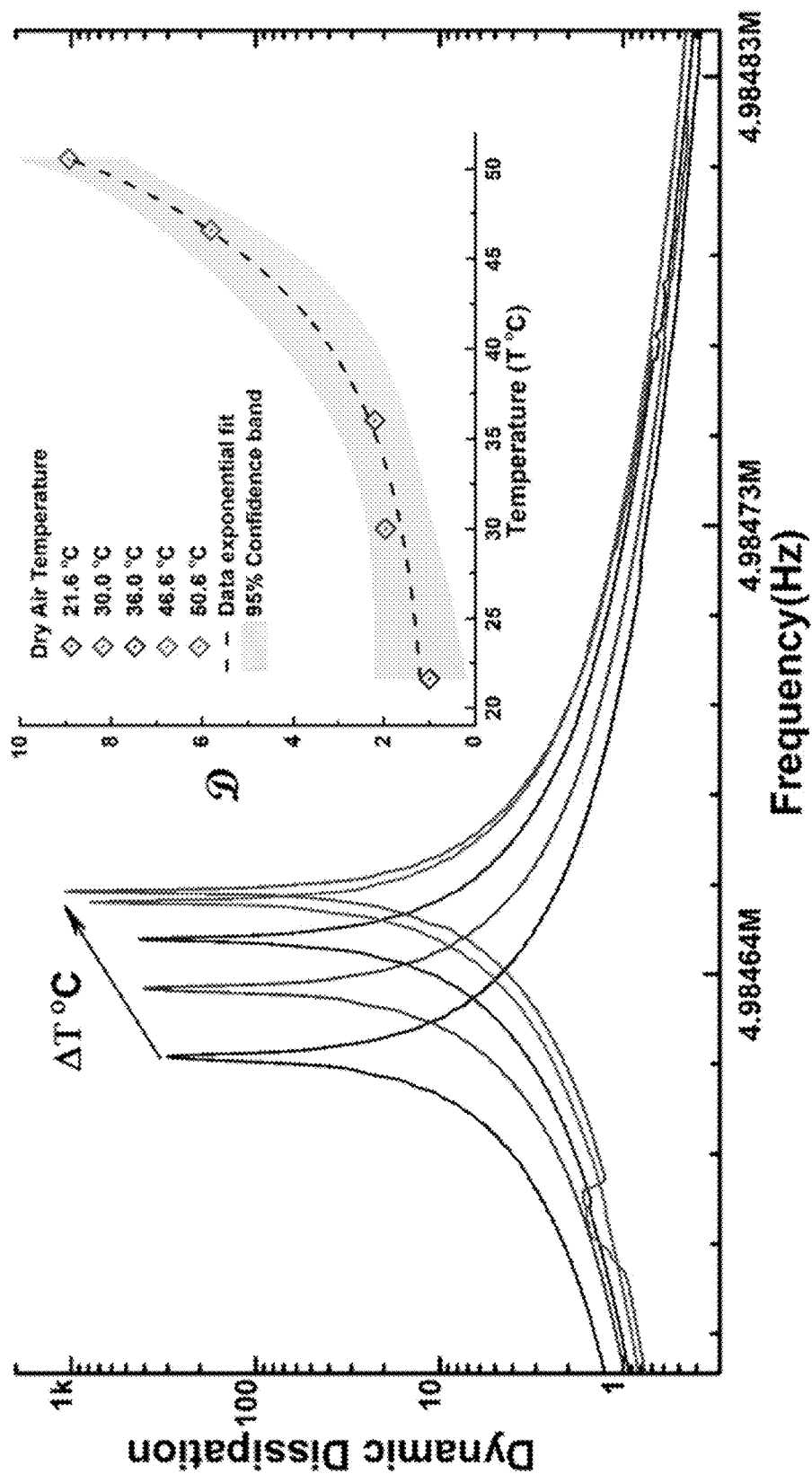
Figure 7A:
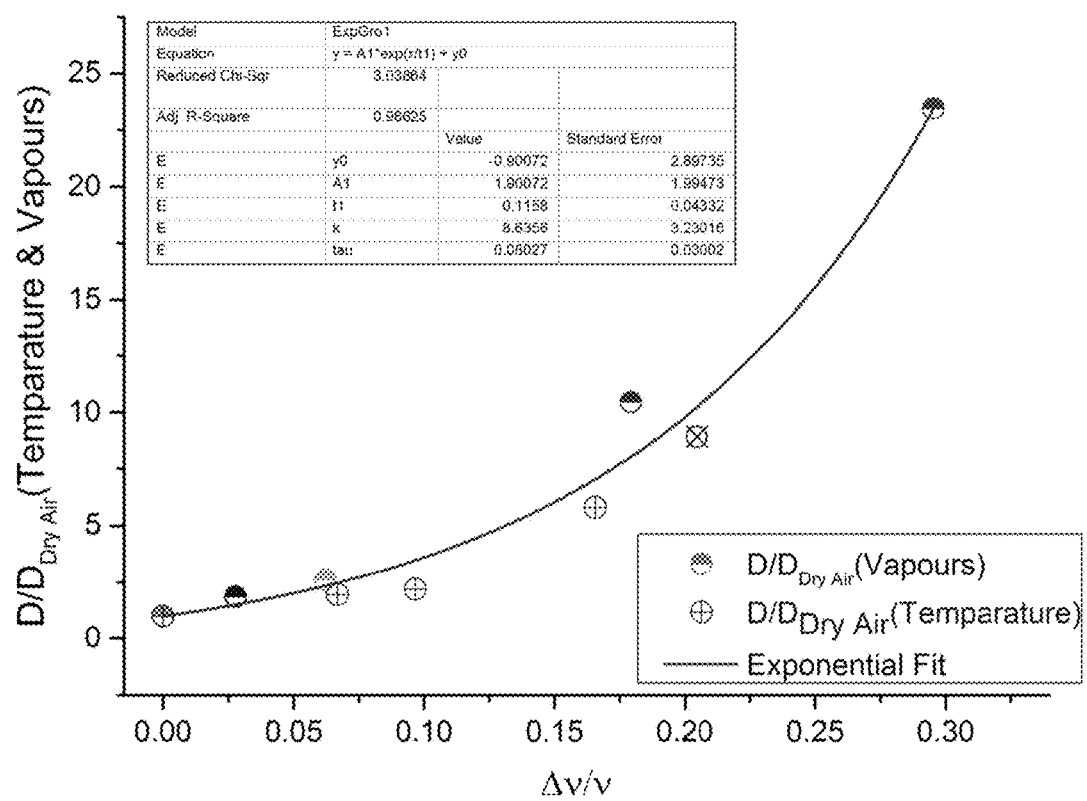
FIGS. 7A and 7B depict the measured dependence of the normalized dissipation as a function of temperature dependent kinematic viscosity change, with the inset in FIG. 7B depicting the data exponential fit and theoretical estimates for the relationship.
Figure 7B:
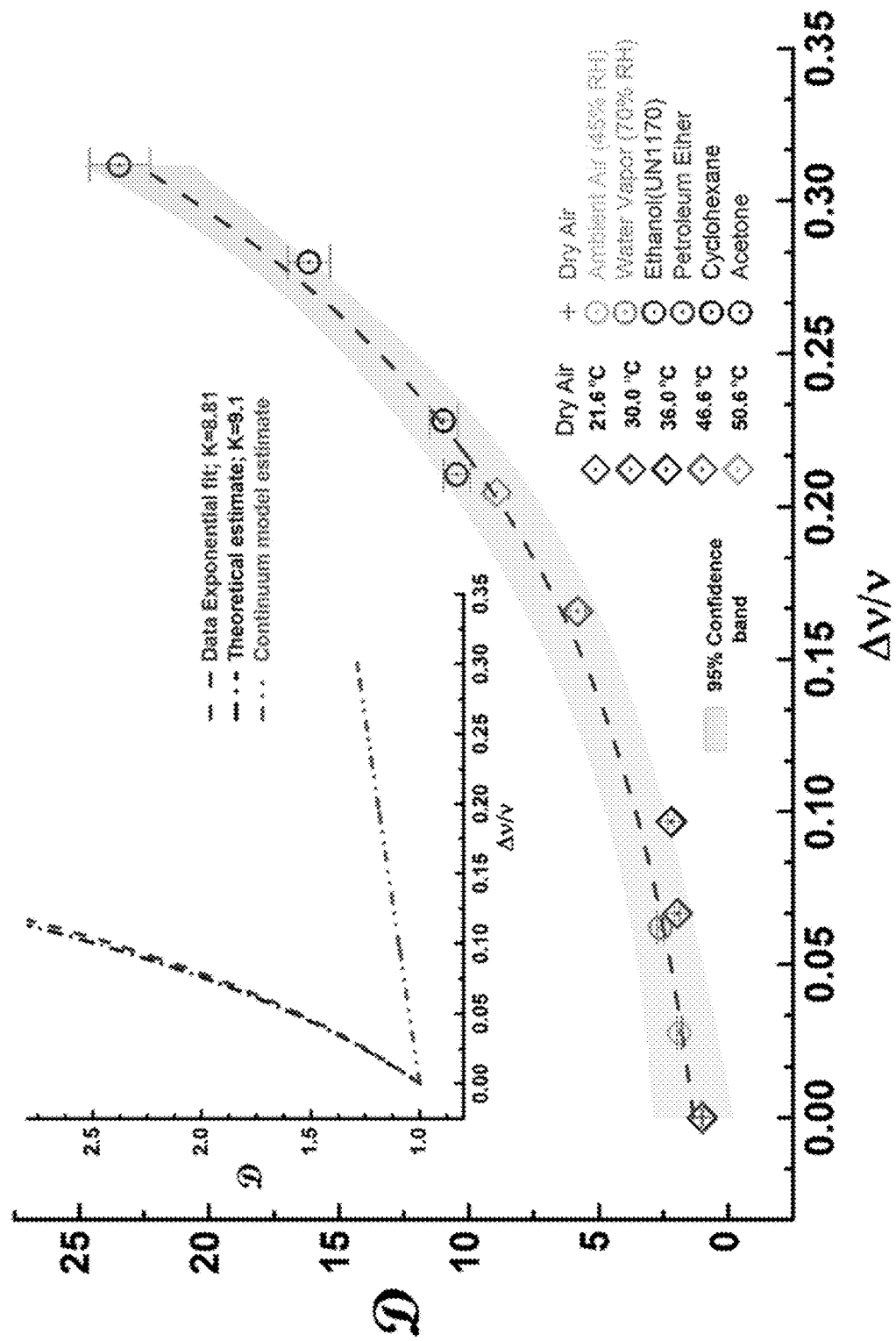

In order to demonstrate that the change in dissipation is caused by the change in kinematic viscosity, an additional series of experiments measuring dissipation of dry air and various media as a function of temperature were performed. The experimental data presented in FIGS. 6A, 6B, 7A, and 7B demonstrates that the dissipation is strongly dependent on the temperature of the ambient media. As shown in the inset of FIG. 6B, the dissipation response of dry air exhibits an exponential trend as a function of temperature. The inset of FIG. 7B demonstrates that the experimental data closely matches the theoretical estimate, and that the Stokes continuum model does not accurately represent the behavior of the sensor.

Figure 8A:
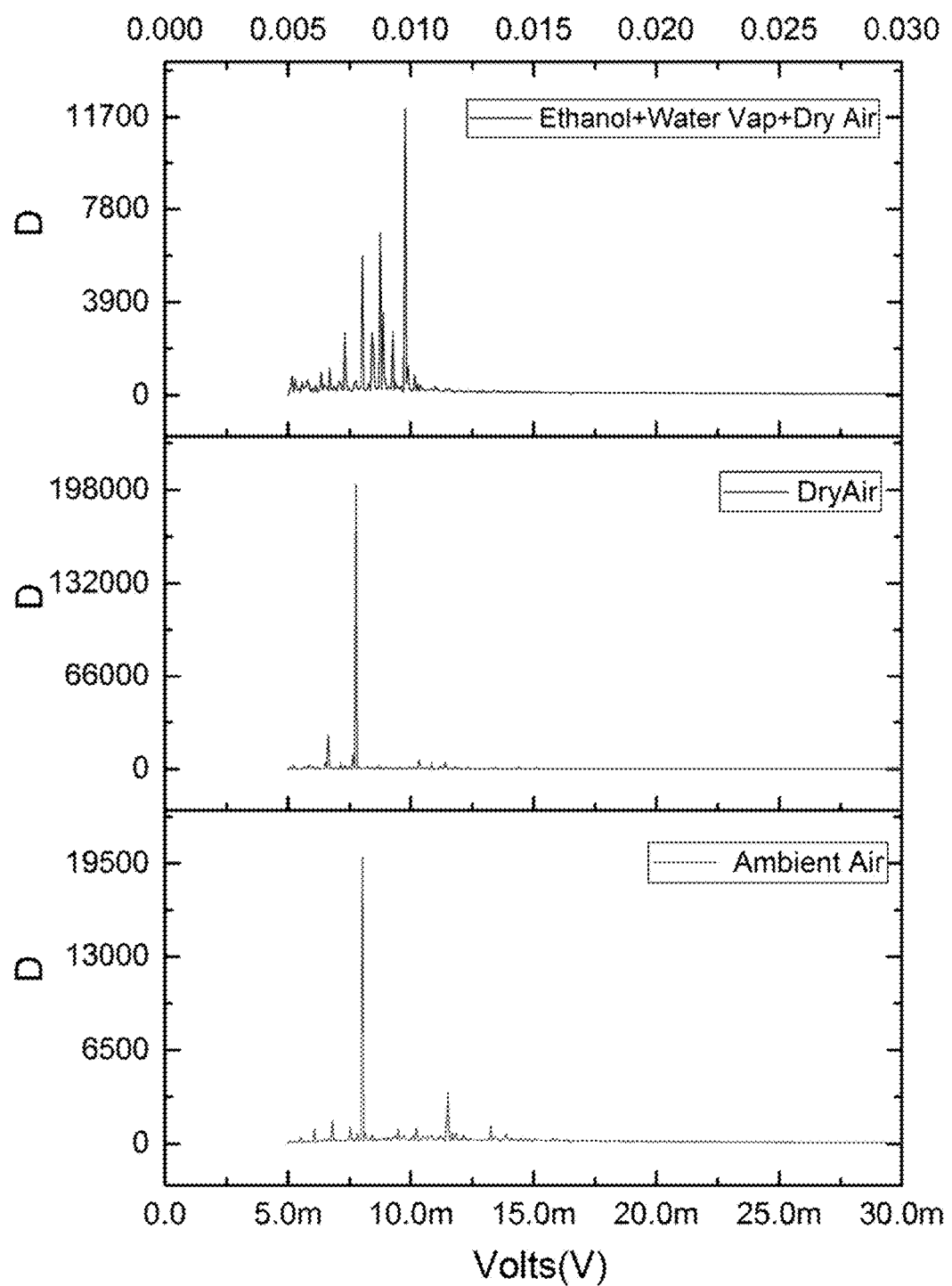
FIGS. 8A and 8B depict the measured dissipation as a function of drive voltage for a variety of media mixtures over a driven amplitude range close to or at the resonance frequency of the oscillator.
Figure 8B:
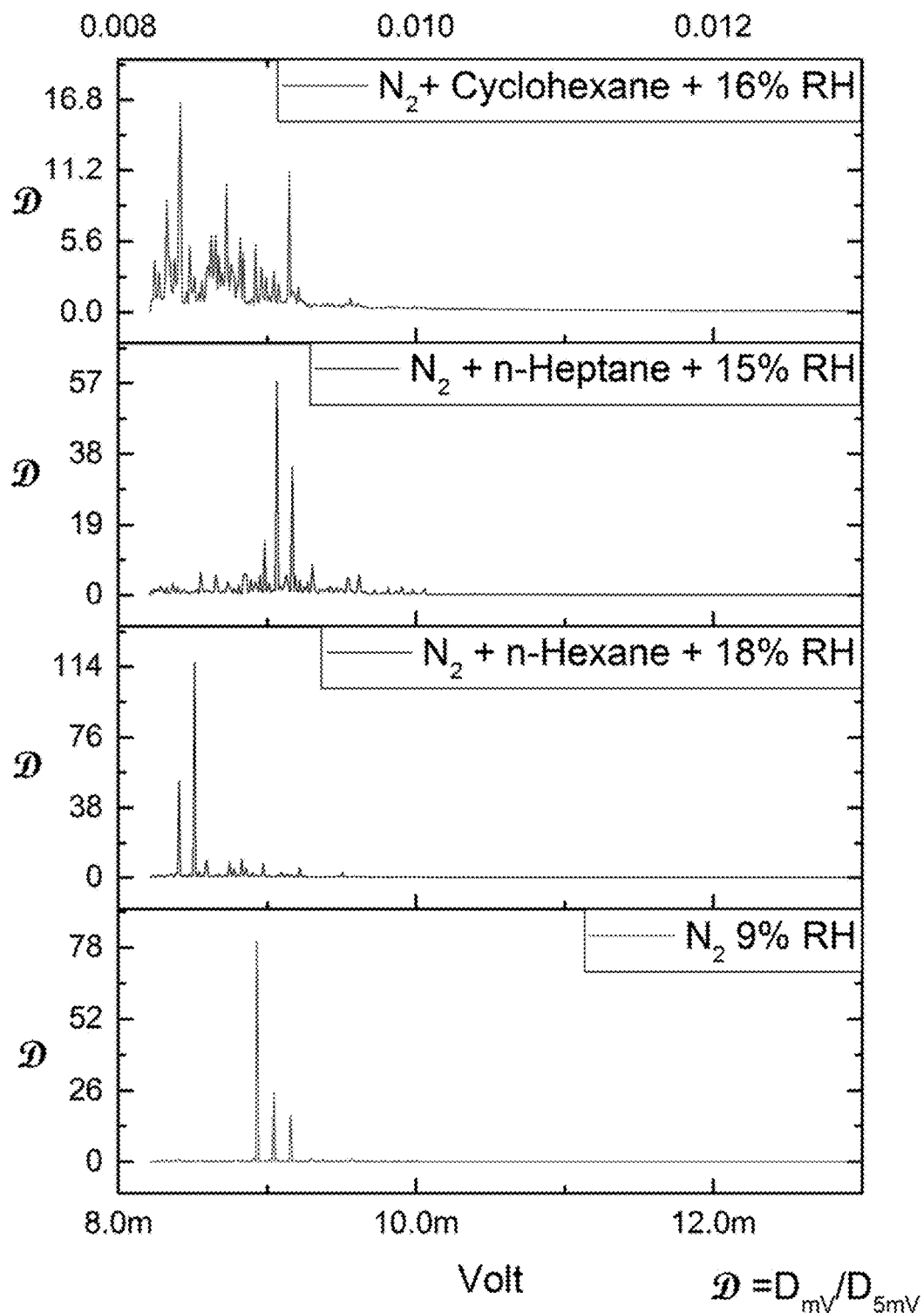

In order to demonstrate the dependence of the dissipation on the driven amplitude of the system, the drive frequency was changed to observe maximum dissipation for a particular drive amplitude (lowest value) in order to probe the presence of resonance frequency for different amplitudes to observe the resulting dissipation peaks for different media components as shown in FIGS. 8A and 8B.

In order to demonstrate that different media produce different characteristic dissipation peaks based upon a driven amplitude of the sensor, the sensor was exposed to different media under the same conditions. The media employed were a combination of ethanol, water vapor and dry air; dry air; ambient air; nitrogen, cyclohexane, and 16% relative humidity; nitrogen n-heptane, and 15% relative humidity; nitrogen, n-hexane, and 18% relative humidity; and nitrogen and 9% relative humidity. As shown in FIGS. 8A and 8B, each of the tested media produced different characteristic dissipation peaks, which may be considered a mechanical dissipation spectrum of the media. The driven amplitude range was 5 mV to 50 my, and was constrained by the equipment employed to obtain the possible resolution of peak positions. Thus, other driven amplitude ranges may be employed with different experimental equipment. The system was operated at or as close as possible to the resonance frequency of the oscillator. Scanning through the amplitudes in the range provide definite dissipation peaks as a function of the driven amplitude. The structure of the peaks may reflect the chemical composition of the media, and correspondingly may be utilized to construct a mechanical spectrum. Thus, the sensor may be employed in a mechanical spectroscopic device. The experimental data shown in FIGS. 8A and 8B is the average of three readings taken for each media, with the time period of each reading corresponding to the time period for which the resonant frequency was stable. The scan period for each amplitude range reading was 45 seconds.

Figure 9:
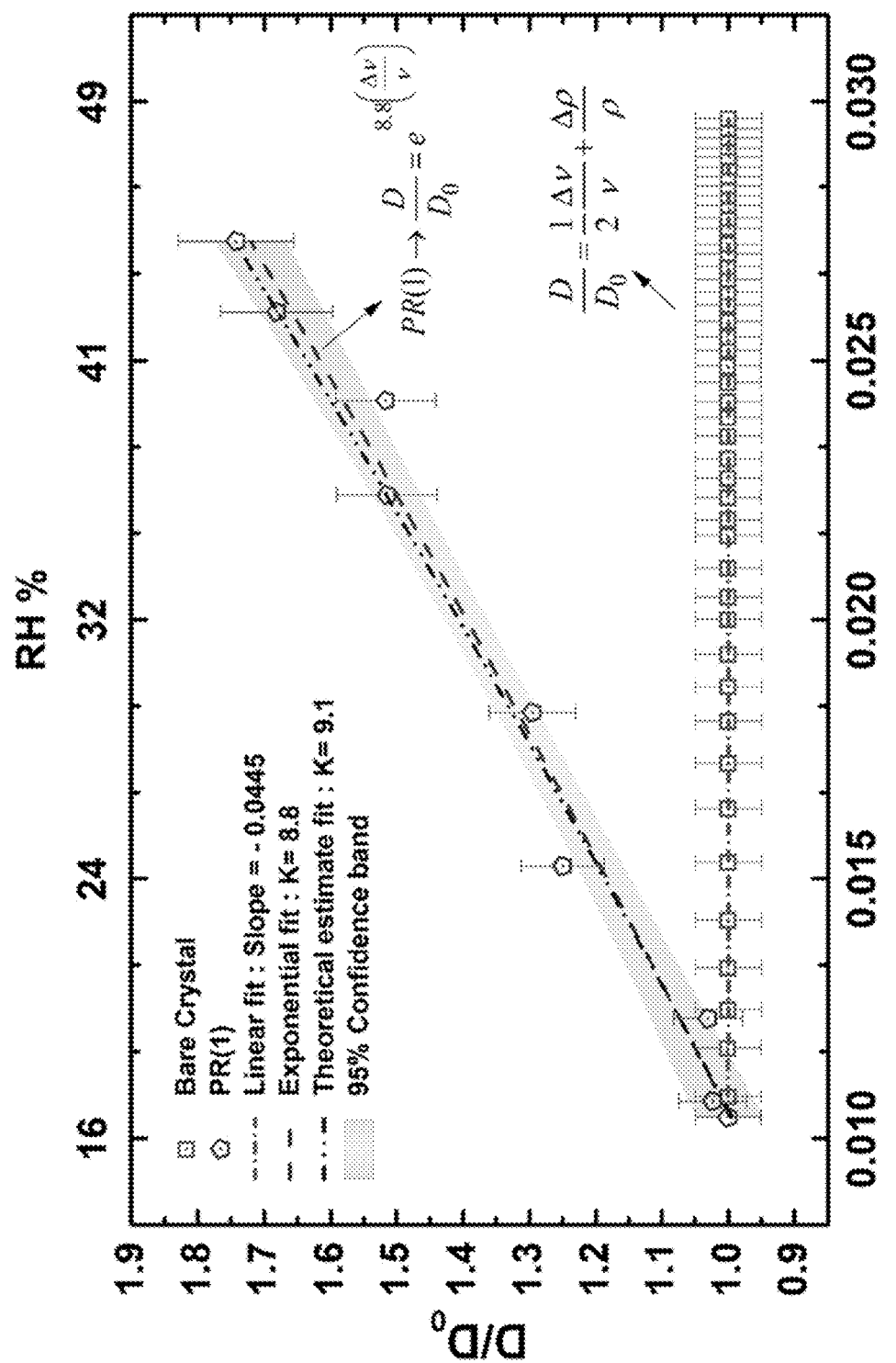
FIG. 9 depicts dissipation as a function of relative humidity (RH) in air for a modified crystal and a bare (non-modified) crystal.

A series of experiments were performed in which the change in the kinematic viscosity with variations in the Relative Humidity (RH) of the media was measured. FIG. 9 depicts the dissipation for a modified crystal (PR(1)) and a bare (unmodified) crystal, with the modified crystal exhibiting an exponential dependence of the kinematic viscosity on RH, while the response for a bare crystal is linear. The result for the bare crystal shown in FIG. 9 is in agreement with theoretical considerations.

Figure 10:
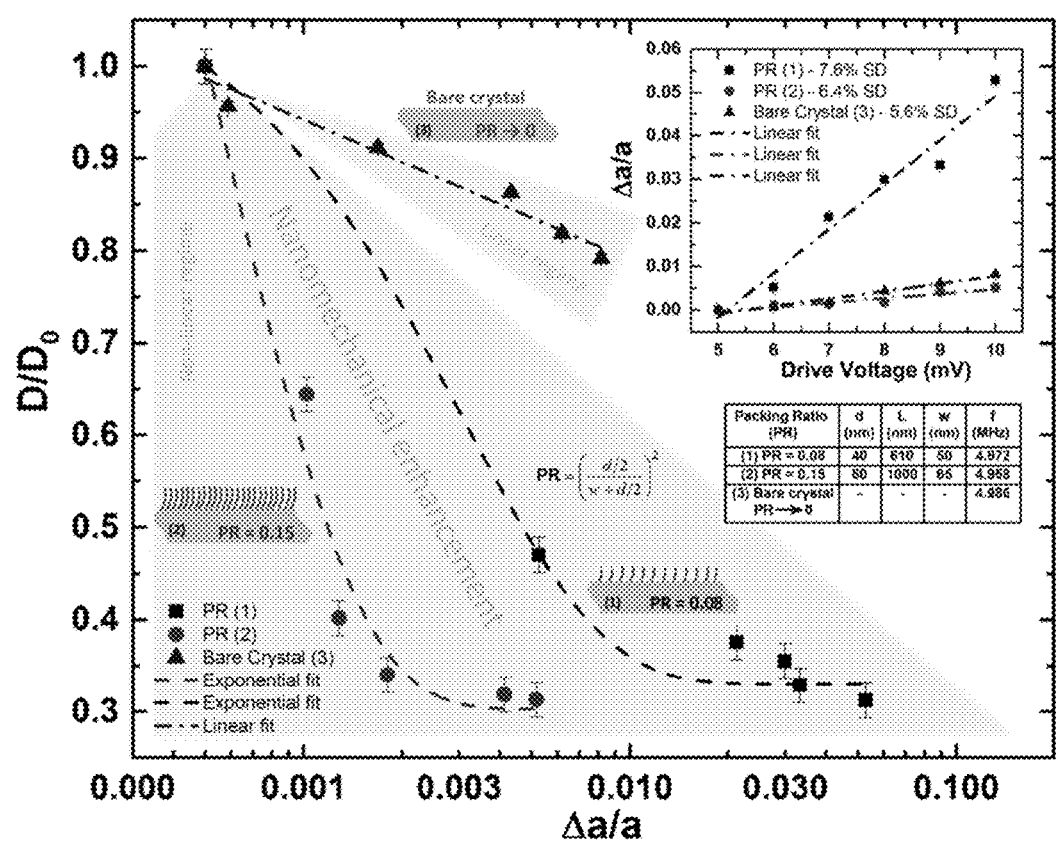
FIG. 10 depicts dissipation as a function of driving amplitude for three different crystals, a bare (non-modified) crystal, and two modified crystals with different nanostructures, the inset depicts the driving amplitude as a function of drive voltage for each crystal.

As shown in FIG. 10, a series of experiments were performed with a bare (unmodified) crystal, a modified crystal with a packing ratio (PR) of 0.08, and a modified crystal with a PR of 0.15. The dissipation was recorded as function of the driving amplitude for each crystal. The bare crystal exhibited a linear response, while the nanostructure modified crystals exhibited a non-linear response. The inset in FIG. 10 depicts the driving amplitude as a function of drive voltage for each crystal.

As utilized herein, the terms "approximately," "about," "substantially," "essentially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

It is important to note that the exemplary embodiments are illustrative only. Although only a few embodiments have been described in detail in this disclosure, those skilled in the art who review this disclosure will readily appreciate that many modifications are possible (e.g., variations in values, manufacturing processes, etc.) without materially departing from the novel teachings and advantages of the subject matter described herein. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

What is claimed:

1. A sensor comprising:
    a resonator;
    a nanostructure comprising a plurality of elements disposed on a surface of the resonator; and
    an impedance analyzer configured to measure dissipation of the plurality of elements of the nanostructure in response to at least one target molecule interacting with the plurality of elements as a media comprising the at least one target molecule flows over the nanostructure without the at least one target molecule attaching to the plurality of elements of the nanostructure, the media comprising at least one of a gas or a vapor;
    wherein the dissipation corresponds to the presence of the at least one target molecule in the media, and wherein an element density of the elements on the nanostructure is in a range of 15 to 25 elements per $\mu m^2$, the element density corresponding to a mean free path of the at least one target molecule in the media.

2. The sensor of claim 1, wherein the resonator is a cut quartz crystal resonator.

3. The sensor of claim 1, wherein the nanostructure is disposed on an electrode surface of the resonator.

4. The sensor of claim 1, wherein the plurality of elements comprises nanotubes or nanorods.

5. The sensor of claim 1, wherein the plurality of elements comprise ZnO nanorods.

6. The sensor of claim 1, wherein the plurality of elements have at least one of:
    a diameter in a range of 20 nm to 60 nm;
    a length in a range of 300 nm to 900 nm; or
    are spaced apart by a distance in a range of 20 nm to 200 nm.

7. The sensor of claim 1, wherein the resonator is disposed within a sensor housing.

8. The sensor of claim 7, wherein the sensor housing includes a sensor chamber, and the plurality of elements extend into the sensor chamber.

9. The sensor of claim 1, further comprising at least one of:
    a heater element configured to increase the temperature of the media to be sensed;
    a humidity source configured to increase the relative humidity of the media to be sensed; or
    an additive gas source configured to increase the amount of an additive gas in the media to be sensed.

10. The sensor of claim 1, further comprising a power source.

11. The sensor of claim 1, wherein the sensor is configured to drive the resonator at a variety of driving amplitudes or frequencies or across a range of driving amplitudes or frequencies.

12. The sensor of claim 1, further comprising an infrared radiation (IR) source configured to irradiate the media to be sensed by scanning through an optical frequency range in the IR spectrum so as to cause an increase in an energy of the at least one target molecule present in the media at a corresponding absorption wavelength of the at least one target molecule so as to increase sensitivity of the nanostructure towards sensing the at least one target molecule.

13. A method of operating a sensor comprising:
    driving a resonator of the sensor at a driving amplitude and frequency such that a nanostructure on a surface of the resonator moves through a media to be sensed, the media comprising at least one of a gas or vapor and having at least one target molecule present therein, an element density of a plurality of elements on the nanostructure being in a range of 15 to 25 elements per $\mu m^2$, the element density corresponding to a mean free path of the at least one target molecule in the media;
    measuring a dissipation response of the resonator in response to the at least one target molecule interacting with the nanostructure as the media flows over the nanostructure without the at least one target molecule attaching to the nanostructure; and
    determining the presence of the component in the media to be sensed based on the measured dissipation response.

14. The method of claim 13, wherein the driving amplitude is 1 mV to 50 mV.

15. The method of claim 13, further comprising heating the media to be sensed to a predetermined temperature before measuring the dissipation response of the resonator.

16. The method of claim 13, further comprising increasing the humidity of the media to be sensed before measuring the dissipation response of the resonator.

17. The method of claim 13, further comprising increasing the content of an additive gas in the media to be sensed before measuring the dissipation response of the resonator.

18. The method of claim 13, wherein determining the presence of a component in the media to be sensed comprises comparing peaks of the measured dissipation response as a function of driving amplitude to known dissipation spectra based on the amplitude.

19. The method of claim 13, further comprising irradiating the media to be sensed with infrared energy by scanning through an optical frequency range in the IR spectrum so as to cause an increase in an energy of the at least one target molecule present in the media at a corresponding absorption wavelength of the at least one target molecule so as to increase sensitivity of the nanostructure towards sensing the at least one target molecule.

* * * * *